United States Patent [19]

Fukukita et al.

[11] Patent Number: 4,787,393
[45] Date of Patent: Nov. 29, 1988

[54] ULTRASONIC TOMOGRAPHIC WITH ALTERNATE IMAGE SCALING

[75] Inventors: Hiroshi Fukukita, Tokyo; Shinichiro Ueno, Machida; Tsutomu Yano, Kawasaki, all of Japan

[73] Assignee: Matsushita Electric Industrial Co., Ltd., Kadoma, Japan

[21] Appl. No.: 932,828

[22] Filed: Nov. 20, 1986

[30] Foreign Application Priority Data

Nov. 20, 1985 [JP] Japan .................................. 60-260027
Apr. 1, 1986 [JP] Japan .................................. 61-74769
Apr. 2, 1986 [JP] Japan .................................. 61-75705

[51] Int. Cl.$^4$ ............................................ A61B 10/00
[52] U.S. Cl. ............................... 128/660.04; 358/112; 128/660.07
[58] Field of Search ................ 340/731, 801; 358/112, 358/287; 128/660-661; 73/620, 625-626

[56] References Cited

U.S. PATENT DOCUMENTS 4,206,654 6/1980 Fukukito et al. ................ 128/660 X
4,241,608 12/1980 Dees et al. ........................ 128/660 X

OTHER PUBLICATIONS

Hoshino et al., "Microprogrammable Ultrasonic Image Processor and Its Applications to Image Manipulation", SPIE, vol. 314, Dig. Radiography, (1981, pp. 354–361).
High Frequency Ultrasonic Imaging of Skin: Experimental Results, Dines et al, "Ultrasonic Imaging", vol. 6, No. 4, pp. 408–434 (1984), Academic Press, Inc.

Primary Examiner—Francis J. Jaworski
Attorney, Agent, or Firm—Cushman, Darby & Cushman

[57] ABSTRACT

An ultrasonic tomographic diagnosis apparatus suitable for skin disease displays a first ultrasonic tomographic image (12) of an object of a fairly broad area, wherein sizes in depthwise direction (X in FIG. 1) displayed in an enlarged scale in relation to sizes in a direction (Y in FIG. 1) on the skin surface, and further a second ultrasonic tomographic image (13) of an object wherein sizes in depthwise direction and sizes in the direction on the skin surface are displayed in substantially proportional to actual size relations, for a selected part marked by a marker (14) on the first tomographic image (12).

While specific embodiments of the invention have been illustrated and described herein, it is realized that modifications and changes will occur to those skilled in the art. It is therefore to be understood that the appended claims are intended to cover all modifications and changes as fall within the true spirit and scope of the invention.

5 Claims, 8 Drawing Sheets

ULTRASONIC TOMOGRAPHIC WITH ALTERNATE IMAGE SCALING

FIELD OF THE INVENTION AND RELATED ART STATEMENT

1. Field of the Invention

The present invention relates generally to an ultrasonic tomograph, and more particularly to an ultrasonic tomograph which is suitable for diagnosis of human skin or a similar organ, through tomographic imaging by utilizing scanning of ultrasonic waves.

2. Background of the Invention

Recently, ultrasonic tomographs using ultrasonic waves of a frequency 20 MHz or higher have been used in the field of diagnosis of skin disease or dermatopathia. These diagnostic techniques require a high image resolution. Such a high frequency ultrasonic tomograph is disclosed, for instance, in the Ultrasonic Imaging (Vol. 6, 408-434, 1984).

When such diagnosis is carried out for human skin by using such a high-frequency-ultrasonic tomograph, a clear imaging of a thickness of at least the epidermis and boundary of at least the epidermis and corium or derma is ncessitated. Such a tomographic image can be obtained by using an ultrasonic transducer device where the ultrasonic transducer element is mechanically linearly driven in a widthwise direction of the human body so that the ultrasonic beam scans a selected area on the skin. An image is displayed, obtained by processing an electric signal based on reflected ultrasonic waves. By utilizing such an ultrasonic tomographic wave of the skin, an initial diagnosis of a skin tumor such as a malignant tumor, or further examination of its detailed nature becomes possible. Generally, the thickness of the epidermis ranges from 0.15 mm of the thicker parts to 0.075 mm of the thinner parts. In order to image such very thin tissue with a good resolution, a very high frequency ultrasonic wave, such as 20 MHz to 40 MHz, should be used. When the frequency of the ultrasonic wave reaches about 40 MHz, however, its attenuation in living tissue becomes very large, and therefore the measurable depth in the human tissue becomes about 1-2 mm. A tomographic image of such human skin is typically displayed on a visual display screen of a visual display apparatus in a manner that a square area on the display screen corresponds to an object region of tomography in the human skin. Moreover, it is desireable to retain the relation of depth vs. scanned length (along the skin surface) as it is. Therefore, the area to be displayed on the display screen becomes about 2 mm in depth x about 2 mm in length in the scanning direction. Accordingly, even though the ultrasonic scanning can cover a longer scanned length on the skin, only one small portion of the scanned area is displayed. In order to display information of a wider range on the skin, it is usual to display the tomographic image by compressing the length along the skin surface in comparison with the depth. Therefore, this conventional tomographic display of the skin expands the displayed image in its depthwise direction in comparison to the size of the scanning length along the skin surface. In order to read the correct size of the actual examined object, scale marks of different pitches for a corresponding length unit, such as 0.1 mm, are displayed on respective directions on the display screen.

Such an ultrasonic diagnostic tomograph apparatus therefore has a tomographic image on the display screen which is displayed in an intentionally distorted shape. Although trained personnel can read and interpret this display, it is distorted and does not show the correct shape. Therefore, when using this device, diagnosis by figure or shape of cells in the tissue of epidermis or corium has been difficult, leading to the possibility of a mistake in diagnosis.

OBJECT AND SUMMARY OF THE INVENTION

The object of the present invention is to provide an ultrasonic diagnosis apparatus capable of displaying ultrasonic tomographic images which makes the diagnosis easier and more correct by displaying tomographic pattern correctly in actual shape without distortion due to elongation in some direction.

The ultrasonic diagnosis apparatus in accordance with the present invention comprises:
visual display means;
first image signal means for producing a first image signal which produces, by means of ultrasonic scanning of an object, a first ultrasonic tomographic image of an object wherein sizes in depthwise direction are displayed in an enlarged scale in relation to sizes in a direction on the skin surface; and
second image signal means for producing a second image signal which produces, by means of the ultrasonic scanning, a second ultrasonic tomographic image of an object wherein sizes in depthwise direction and sizes in the direction on the skin surface are displayed substantially proportional to actual size relations.

DETAILED DESCRIPTION OF THE PREFERRED EMBODIMENT

A preferred embodiment of the present invention will be described with reference to the accompanying drawings.

Figure 1:
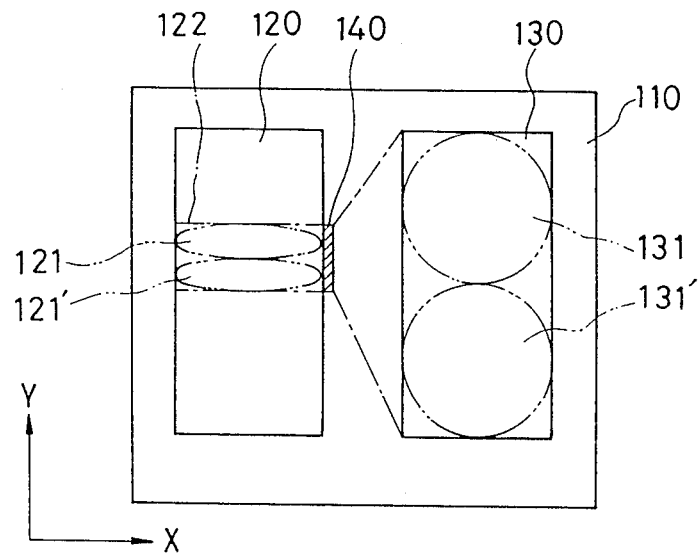
FIG. 1 is a front view showing one example of displayed images of one embodiment of the ultrasonic tomograph in accordance with the present invention.

FIG. 1 is a front view showing one example of displayed images of one embodiment of the ultrasonic tomograph embodying the present invention, as it would be displayed on a display screen. FIG. 1 shows a first region 120 in a leftmost portion including first tomographic images 121 and 121', and a second region 130 in a right portion including second tomographic images 131 and 131'. First region 120 includes small part area 122 which is enlarged in the vertical direction in comparison with the horizontal direction on the display screen.

In both the first tomographic images 121 and 121' in the first region, 120, and the second tomographic images 131 and 131' in the second region 130, the vertical direction (Y axis) represents a distance along the skin surface of a line of scanning of an ultrasonic wave, and the horizontal direction (X axis) represents a depth from the skin surface. The embodiment of FIG. 1 shows the shape of the first and second regions 120 and 130 being the same. However, the vertical size (Y direction) may have a scale which is as large as double that of the scale of length of the size in the horizontal direction (X direction). On the other hand, the actual length of scanning on the skin surface corresponding to the vertical length of the first region 120 for the first tomographic image 121 is 10 mm and the actual depth from the skin surface corresponding to horizontal length of the first tomographic image 12 is 1 mm. However, the actual length of scanning on the skin surface corresponding to the vertical length of the second region 130 for the second tomographic image 121 is 2 mm, which is a one-fifth scale portion in the vertical direction of the 10 mm vertical length, and the actual depth from the skin surface corresponding to the second part 130 is also 1 mm. For instance, the second tomographic image 131 shown in the second region 130 corresponds to the 2 mm length (in the scanning direction)×1 mm depth part of the skin. This part is represented in the first region 120 as a horizontally oblong region 122 whose width (in the vertical direction) is marked by a shaped portion of a display marker 140 on the display screen 110. Region 122 is defined as a rectangle bounded by the display marker 140 and can move in the first region 120.

In the above-mentioned configuration of the display screen, 1 mm of actual length in the direction of scanning on the skin surface is represented at a 1/10 scale in the vertical (Y) direction in the first region 120, and 1 mm of length in the depthwise direction is represented in the first region 120 as its full length in the horizontal (X) direction.

Due to this difference in scale in the X and Y directions of the first region 120, for example, two ball-shaped matters, will be assumed to be buried in series in the scanning direction in the above-mentioned 2 mm region of skin immediately below the skin surface. These balls will be displayed, however, not as round balls in first region 120, but as two horizontally oblong elliptically shaped first tomographic images 121, 121'. The same ball-shaped matters, however, are represented as two vertically disposed circles of the second tomographic image 131 in the second region 130 of the display screen 110. This is because the second tomographic image is that portion which represents a vertically expanded, by a factor of five times, figure of the first tomographic image at the area marked by the marker 140. That is, the image of the second region has a five-times expanded vertical (Y) length as compared with the region 122 marked by the marker 140. In the second region 130, an actual length of 1 mm in the scanning direction (Y) corresponds to one half of the vertical length (representing a 2 mm length part on the skin) of the second region 130.

As described above, since the second region 130 shows a tomographic image produced by vertically enlarging rection 122 of first region 120, which itself represents the tomographic information in a vertically compressed manner, the second tomographic image 131 represents the actual tomographic information in its natural shape as it exists in the skin.

Accordingly, the ultrasonic tomograph of the present invention advantageously represents such an object which has a wide area over a scan of a very small depth thereof, such as human skin. The doctor can make an accurate diagnosis by easily reading the tomographic image in its actual proportional shape. Therefore, mistakes in diagnosis can be easily prevented because the actual shapes can be seen, and a finding of doubtful parts on the skin surface is facilitated by utilizing display marker 140 which points to second region 130.

Figure 2:
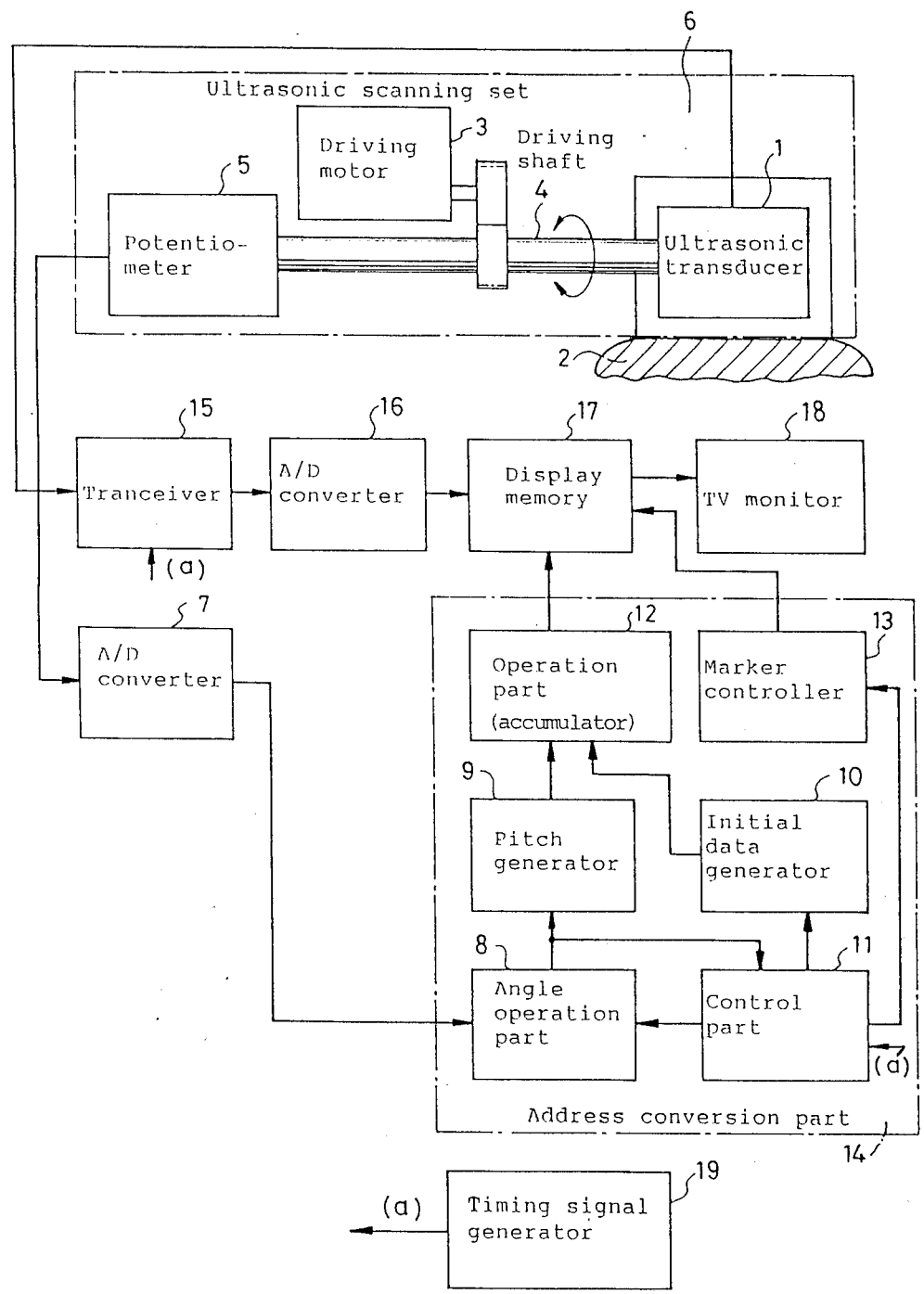
FIG. 2 is a circuit block diagram of a first embodiment of the ultrasonic tomograph of the present invention.

FIG. 2 is a circuit block diagram for realizing the dual tomographic image expression as shown in FIG. 1. An ultrasonic beam is emitted from an ultrasonic transducer 1 onto the object to be examined 2, and an ultrasonic wave is reflected by object 2. Information of the scanning angle of the ultrasonic transducer 1 is produced from ultrasonic scanning set 6. The ultrasonic transducer 1 is driven in a sector scanning manner in a certain limited angle, such as within 90° angle, by a driving motor 3 and through a driving shaft 4. A transceiver 15 is connected to the ultrasonic transducer 1 so that, based on a timing signal shown by arrow (a) given, from a timing signal generator 19, the transceiver 15 intermittently transmits an ultrasonic signal to the ultrasonic transducer 1, which in turn produces ultrasonic waves. The ultrasonic wave reflected by the object to be examined 2 is received by the ultrasonic transducer 1, which converts the reflected ultrasonic wave to an electric signal (a received signal) which is routed to the transceiver 15. The transceiver 15 amplifies the electric signal and provides the amplified signal to an A/D converter 16, whic converts the amplified received signal to a digital-type signal. An electric signal representing the angular position of the ultrasonic transducer 1 is produced by a potentiometer 5 which is coupled to the driving shaft 4. This signal representing the angular motion (hereinafter referred to as the angular signal) is routed to an A/D converter 7, which converts the signal given thereto in synchronism with timing signal (a) from the timing signal generator 19. A/D converter 7 issues a digital-converted angular signal to an address conversion part 14.

The digital-converted signal from the A/D converter 16 is stored in a display memory 17 in a form such that each signal is associated with a digital-converted angular signal from the A/D converter 7 as described in the following. Image data issued from the display memory is given to a TV monitor 18 to display the tomographic image as shown in FIG. 1.

The digital-converted angular signal from the A/D converter 7 is provided to an angle operation part 8 which is controlled by a signal given from a control part 11 (described herein). Angle operation part 8 issues various compression data to a pitch generator 9 to define selected compression angle ranges (e.g. 18°) which are 1/N (e.g. 1/5) of the of the whole scanning angle, such as 90°. In this embodiment, the display memory 17 is designed such that all of the digital information which is obtained from the A/D converter 16 of the reflection signal for the whole range of the scanning angles of the ultrasonic transducer 1 can be stored therein. The control part 11 issues control signals for various N-numbers. The output of the angle operation part 8 is then converted by the pitch generator 9 to pitch data $X_p$ and $Y_p$. At the same time, an initial data generator 10, also controlled by control part 11, issues initial data $X_s$ and $Y_s$. By receiving the pitch data $X_p$ and $Y_p$ from the pitch generator 9 and receiving initial data $X_s$ and $Y_s$ from the initial data generator 10, an operation part 12 produces address data $X_a$ and $Y_a$ for the X coordinate and Y coordinate in the display memory 17 as follows:

$X_a = X_s + M \cdot X_p$ $Y_a = Y_s + M \cdot X_p,$ wherein M is a number to designate the M-th output data of the A/D converter 16 in transmission timing for each pixel of the TV monitor 18. The data and address are provided in the above-mentioned manner to the display memory 17 to constitute the tomographic image thereby. In case the angle operation part 8 does not compress the angle data, that is the case of displaying the tomographic image without a vertical compression of the image in comparison with the actual configuration, only one part of the whole scanning range is read out from the display memory. The reset of the parts of the display memory then have addresses which exceed the addresses of the display memory 17, and the display operation for such exceeding address is not possible. However, by appropriately selecting initial addresses $X_s$ or $Y_s$, writing in the display memory of desired parts of the whole scanning range becomes possible. In the manner of displaying as shown in FIG. 1, by adjustment of the initial data $Y_s$, the scanning range to be displayed is designated; and further, by adjusting the initial data $X_s$, selection of the part to be displayed in the horizontal direction (left, central or right part) is designated.

At the same time, the control part 11 issues data for display marker 140 of FIG. 1 which designates the part to be displayed as second tomographic image 131 in second region 130 in the display screen 110 and writes data indicative of the display marker 140 in the display memory 17.

In the above-mentioned embodiment, designation of the selected part (marked part) which is to be displayed in actual proportion in the second tomographic image in second region 130 is made at the time of storing the data in the display memory 17. However, other configurations are possible, such that the memory capacity of the display memory 17 is increased and tomographic image data is stored for the whole scanning range, so as to enable a display of the actually proportioned tomographic image (not vertically compressed). Thereby, by means of controlling addresses in the reading and displaying the vertically compressed first tomographic image in the first region 120 by abridged data (e.g. one line in every five lines), a displaying of the actually proportioned second tomographic image 3 is made by reading out the whole data in the selected scanning range designated by the display marker 140.

Figure 4:
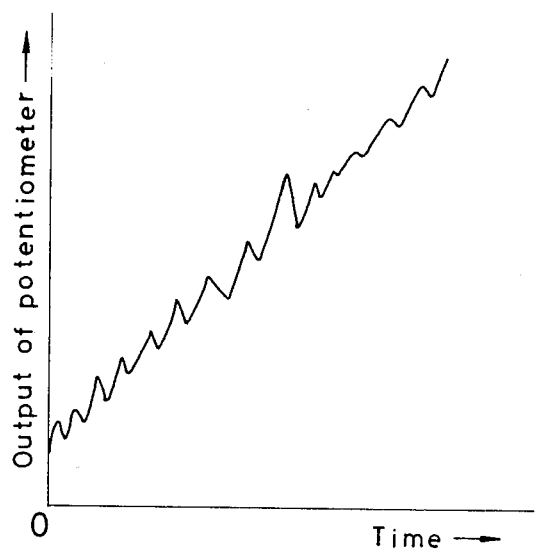
FIG. 4 is a graph showing an example of an output voltage from a potentiometer of the embodiment of FIG. 4.
Figure 5:
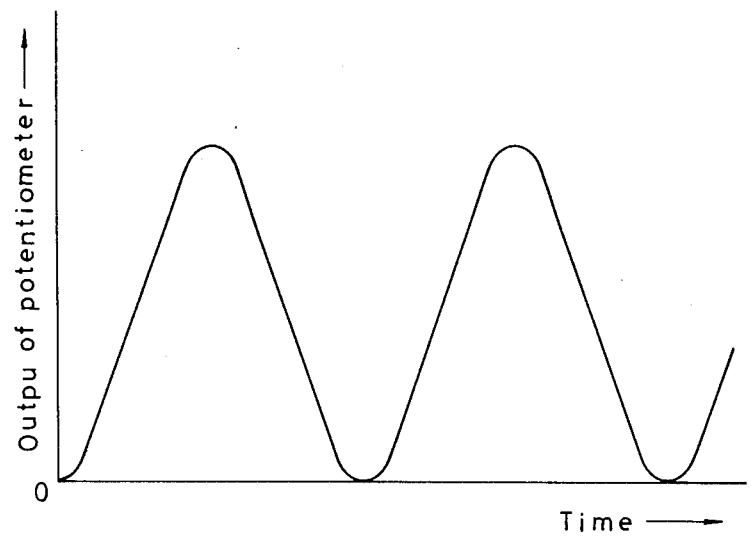
FIG. 5 is a graph showing the output voltage of another potentiometer for use in place of the potentiometer of FIG. 4.

A second embodiment is described with reference to FIG. 3, FIG. 4 and FIG. 5. This embodiment is devised so as to eliminate any undesirable noise in the output signal of the potentiometer, thereby affording a reliable tomographic image display suitable for surgical diagnosis. In the aforementioned embodiment of FIG. 2, a direct analog output signal of the potentiometer 5 is used as the angular signal which is to be inputted to the A/D converter 7. Accordingly, when some noise or fluctuation occurs in the analog output signal of the potentiometer 5, the digital-converted output of the A/D converter 7 may produce an unreliable digital angular signal. Therefore, this converted digital signal is stored in display memory 17. If such an angular signal is utilized for displaying the tomographic images, wrong addresses may be read out and displayed on display screen 110, and hence a wrong or unreliable tomographic image may be displayed. In other words, the accuracy and reliability of the angular information is very important for making a reliable tomographic image. Without such reliable angular information, the tomographic image may include defects or dropouts of the image. In order to solve such a problem, this second embodiment described with reference to FIG. 3, FIG. 4 and FIG. 5 provides an ultrasonic tomograph wherein reliability of the tomographic image is improved by obtaining very accurate and reliable angular information of the sector scanning.

Figure 3:
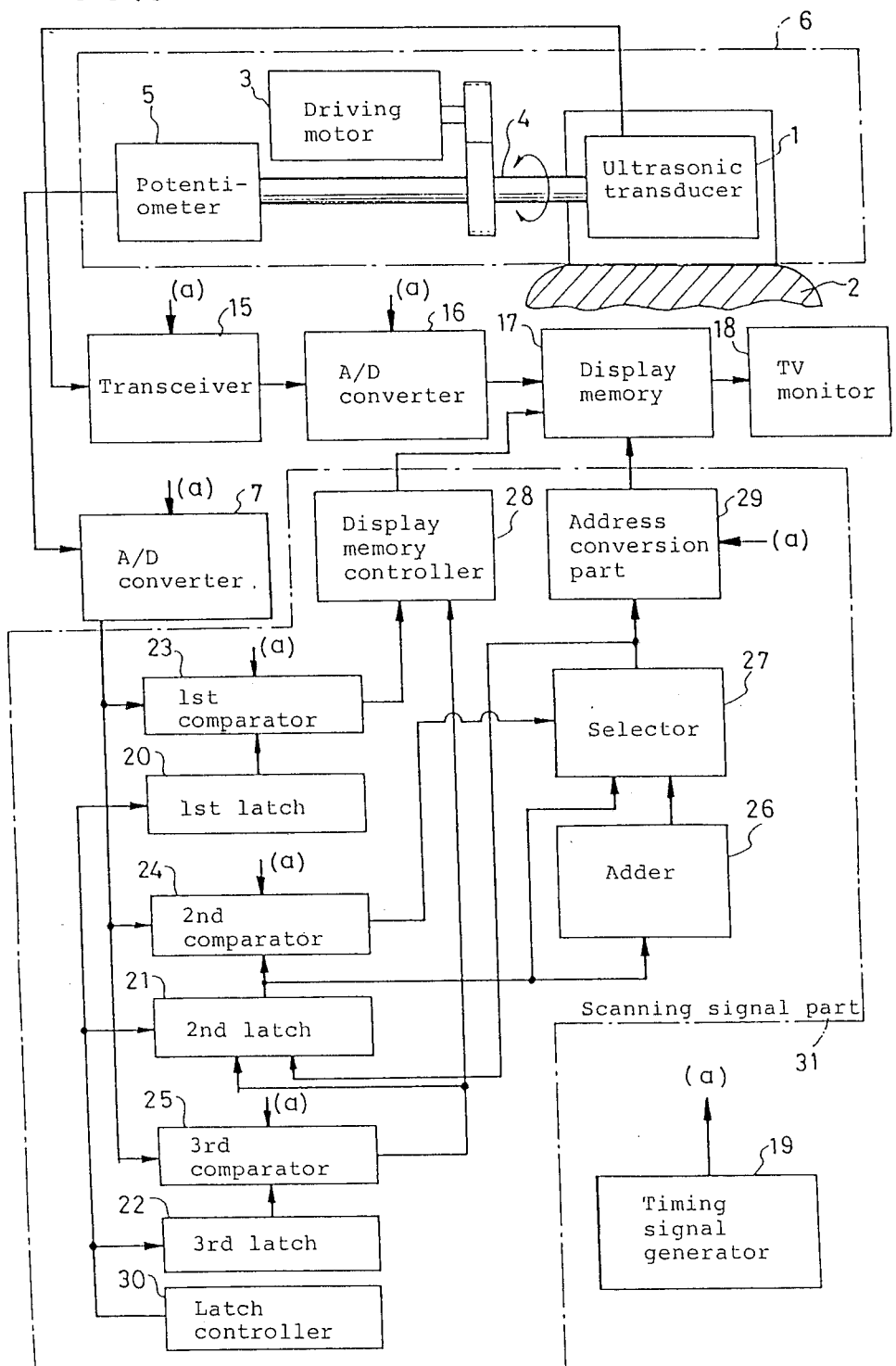
FIG. 3 is a circuit block diagram of another embodiment of the ultrasonic tomograph of the present invention.

In the circuit block diagram of FIG. 3, an ultrasonic beam is emitted from an ultrasonic transducer element 1 onto the object to be examined 2, and an ultrasonic wave is reflected by the object 2. Information on the scanning angle of the ultrasonic transducer element 1 is issued from ultrasonic scanning set 6. The ultrasonic transducer 1 is driven in a sector scanning manner in a fan shape range of a certain limited angle, such as within a 90° angle, by a driving motor 3 and through a driving shaft 4. A transceiver 15 is connected to the ultrasonic transducer 1 so that, based on a timing signal (a) from a timing signal generator 19, the transceiver 15 intermittently transmits an ultrasonic signal to the ultrasonic transducer 1, which produces an ultrasonic wave in response. The ultrasonic wave reflected by the object to be examined 2 is received by the ultrasonic transducer 1, which converts the reflected ultrasonic wave to an electric signal which is provided to the transceiver 15. Then, the transceiver 15 amplifies the electric signal (hereinafter referred to as received signal) and routes it to an A/D converter 16, which converts the received signal to a digital-type signal. An electric signal representing the angular position of the ultrasonic transducer 1 is produced by a potentiometer 5 which is coupled to the driving shaft 4. This signal representing the angular motion (hereinafter referred to as angular signal) is provided to an A/D converter 7, which converts the signal given thereto in synchronism with timing signal (a) from the timing signal generator 19 and to issue digital-converted angular signal to scanning signal part 31.

The digital-converted received signal from the A/D converter 16 is stored in the display memory 17 in a form combined with the digital-converted angular signal from the A/D converter 7 as described in the following. Image data issued from the display memory is given to a TV monitor 18 to display the tomographic image as shown in FIG. 1.

Selected ones of the digital-converted angular signals from the A/D converter 7 are latched into first latch 20, second latch 21 and third latch 22. These latches store values to be compared with the current output signal from the A/D converter 7. A first comparator 23, a second comparator 24, and a thid comparator 25 are provided for comparing current output signals from the A/D converter 7 with values retained in the first latch 20, the second latch 21 and the third latch 22, respectively. The output of the second latch 21 is given to an adder 26 and to a selector 27, which also receives the output from the adder 26. Outputs of the first comparator 23 and the third comparator 25 are provided to a display memory controller 28, which issues control output signals to the display memory 17. The output of the selector 27 is given to an address conversion part 29, which provides an address conversion signal to the display memory 17. This output of selector 27 is also provided to the second latch 21. The address conversion part 29 adjusts the angular information of the scanning angle of the ultrasonic transducer element 1 to address matrix disposition in the display memory 17. A latch controller 30 gives signals to the first latch 20, the second latch 21 and the third latch 22 to control them to preliminarily retain predetermined values therein. The above-mentioned component circuits, namely the latches 20, 21 and 22, the comparators 23, 24 and 25, the adder 26, the selector 27, the address conversion part 29 and the latch controller 30 constitute the scanning signal part 31. The component circuits in the scanning signal part 31 have their operation timing controlled by a timing signal given from a timing signal generator 19. The storing of the tomographic image data obtained from the ultrasonic transducer element 1 into display memory 17 is substantially the same as already described in the first embodiment circuit with reference to FIG. 2, and therefore any elucidation thereof is omitted for simplicity.

Now, the processing of output of the potentiometer 5 for improving reliability of the tomographic image is elucidated in detail hereafter.

The current output of the A/D converter 7 is compared with predetermined values retained by the first latch 20, the second latch 21 and the third latch 22, by three comparators—the first comparator 23, the second comparator 24 and the third comparator 25, respectively. The first, scond and third latches 20, 21 and 22 retain predetermined values under control of latch controller 30. The latch 21 initially has the same value as the first latch 20.

An elucidation will first be made for displaying the ultrasonic tomographic image when the analog output signal of the potentiometer 5 increases. In the first latch 20, a value corresponding to an angle of display starting is retained, and in the third latch 22 an angle of display finish is retained, under control of the latch controller 30. The value stored in the first latch 20 is selected to be smaller than the value stored in the third latch 22. First, the display memory controller 28 issues a signal to prohibit the writing of the received signal in the display memory 17. The output of the A/D converter 7 is then compared with the value of the first latch 20 in the first comparator 23, in synchronism with the timing signal (a) issued from the timing signal generator 19. When these two values agree with each other, or when the output of the A/D converter 7 is larger than the value of the first latch 20, the first comparator 23 issues a signal to the display memory controller 28. Upon reception of the signal, the display memory controller 28 switches from the previously issued writing-prohibition signal to a writing start signal, to enable writing of the received signal from the A/D converter 16 into the display memory 17. Thereafter, the display memory controller 28 retains the writing start signal. The current output of A/D converter 7 is thereafter compared with the value of the second latch 21 in the second comparator 24, in synchronism with the timing signal (a) from the timing signal generator 19. The second latch 21 initially retains the same value as that retained in the first latch 20. The adder 26 always holds a value that is equal to a value of the second latch 21 but with a certain value, for instance 1, added thereto. By comparing the above-mentioned two values, the second comparator 24 issues different control signals to the selector 27 depending on whether the output of the A/D converter 7 is larger than the value of the second latch 21 or not. Upon reception of such signal, the selector 27 provides the output of the adder 26 to the address conversion part 29 when the output of the A/D converter 7 is larger than the value of the second latch 21, or issues the output of the second latch 21 directly to the address conversion part 29 when the case is other than the above. The address conversion part 29 provides an output in the form of angle information which matches with matrix disposition of the display memory 17, in synchronism with the timing signal (a) from the timing signal generator 19, and provides this output to the display memory 17. Furthermore, by means of the angle information, the received signal which is given from the A/D converter 16 is written into the display memory 17. The output of the selector 27 is written in the second latch 21 in synchronism with the timing signal (a) from the timing signal generator 19. The output of the A/D converter 7 is then compared with the value in the third latch 22 in the third comparator 25, in synchronism with the timing signal (a) from the timing signal generator 19. When the comparison results in an equality of the two values, or when the output of the A/D converter 7 is larger than the value of the third latch 22, a signal which shifts the output of the display memory controller 28 to a signal to prohibit the writing in the display memory 17 is issued from the third comparator 25. At that time, the value of the second latch 21 is shifted back to the value of the first latch 20 by this signal, and the whole circuit is restored to its initial state, and the output of the A/D converter 7 and the value of the first latch 20 are compared with each other again. By reporting the above-mentioned steps, the ultrasonic tomographic image displayed on the TV monitor 18 can be refreshed.

FIG. 4 shows an output signal of the potentiometer 5 having irregular (non-monotonous) changes induced by, for instance, noise. In this case, input values of an address conversion part 29 become the basis of the angular information, and are processed by smoothing by the scanning signal part 31. Outputs of the non-processed A/D converted value issued directly from the A/D converter 7 are shown in Table 1. In this table, the values retained by the first and second latches are initially 10 and 246, respectively.

TABLE 1

| Output of value of A/D converter 7 | Value of output of second latch 21 | Value of output of adder 26 | Control signal to display memory | Smoothing processed input value to address conversion part 29 |
|---|---|---|---|---|
| 9 | 10 | 11 | | |
| 8 | 10 | 11 | Prohibit | |
| 9 | 10 | 11 | | |
| 10 | 10 | 11 | | 10 |
| 15 | 10 | 11 | | 11 |
| 11 | 11 | 12 | Start | 11 |
| 11 | 11 | 12 | | 11 |
| 12 | 11 | 12 | | 12 |

TABLE 1-continued

| Output of value of A/D converter 7 | Value of output of second latch 21 | Value of output of adder 26 | Control signal to display memory | Smoothing processed input value to address conversion part 29 |
|---|---|---|---|---|
| 13 | 12 | 13 | | 13 |
| 15 | 13 | 14 | | 14 |
| 16 | 14 | 15 | | 15 |
| 18 | 15 | 16 | | 16 |
| 18 | 16 | 17 | | 17 |
| 18 | 17 | 18 | | 18 |
| 20 | 18 | 19 | | 19 |
| 19 | 19 | 20 | | 19 |
| 20 | 19 | 20 | | 20 |
| 22 | 20 | 21 | | 21 |
| . | . | . | | . |
| . | . | . | | . |
| . | . | . | | . |
| 243 | 243 | 244 | | 243 |
| 242 | 243 | 244 | | 243 |
| 244 | 243 | 244 | | 243 |
| 243 | 243 | 244 | | 243 |
| 245 | 243 | 244 | | 244 |
| 245 | 245 | 246 | | 245 |
| 248 | 245 | 246 | Prohibit | |

N.B. The value retained in the first latch 20 is 10, and the value retained in the third latch 22 is 246.

As is obvious from the above-mentioned Table 1, the output of second latch 21 assumes all values between the values of the first and third latches. When the output of A/D converter has an error due to the noise, the input data to address conversion part 29 is corrected. Therefore, the angular information is processed to remove all possible defects, including abrupt changes or dropouts in the digitalized angular data for a monotonous angular motion of the scanning, and the processed angle information in full is stored in the display memory. This enables, in reading out the tomographic imaging data from the memory, a reliable ultrasonic tomographic image.

When the output of the potentiometer 5 repeatedly increases and decreases, as illustrated in FIG. 5, the similar smoothing processing of the angular information as in the above example can also be realized by alternately making the increasing operation and decreasing operation.

By utilizing the above-mentioned circuit configuration of FIG. 3, even when the analog output of the potentiometer 5 has such irregular or abrupt changes from the intended monotonous change of angle information, a smoothly continuing angle information without any defects or dropouts can be realized, thereby enabling production of a reliable ultrasonic tomographic image.

Figure 6:
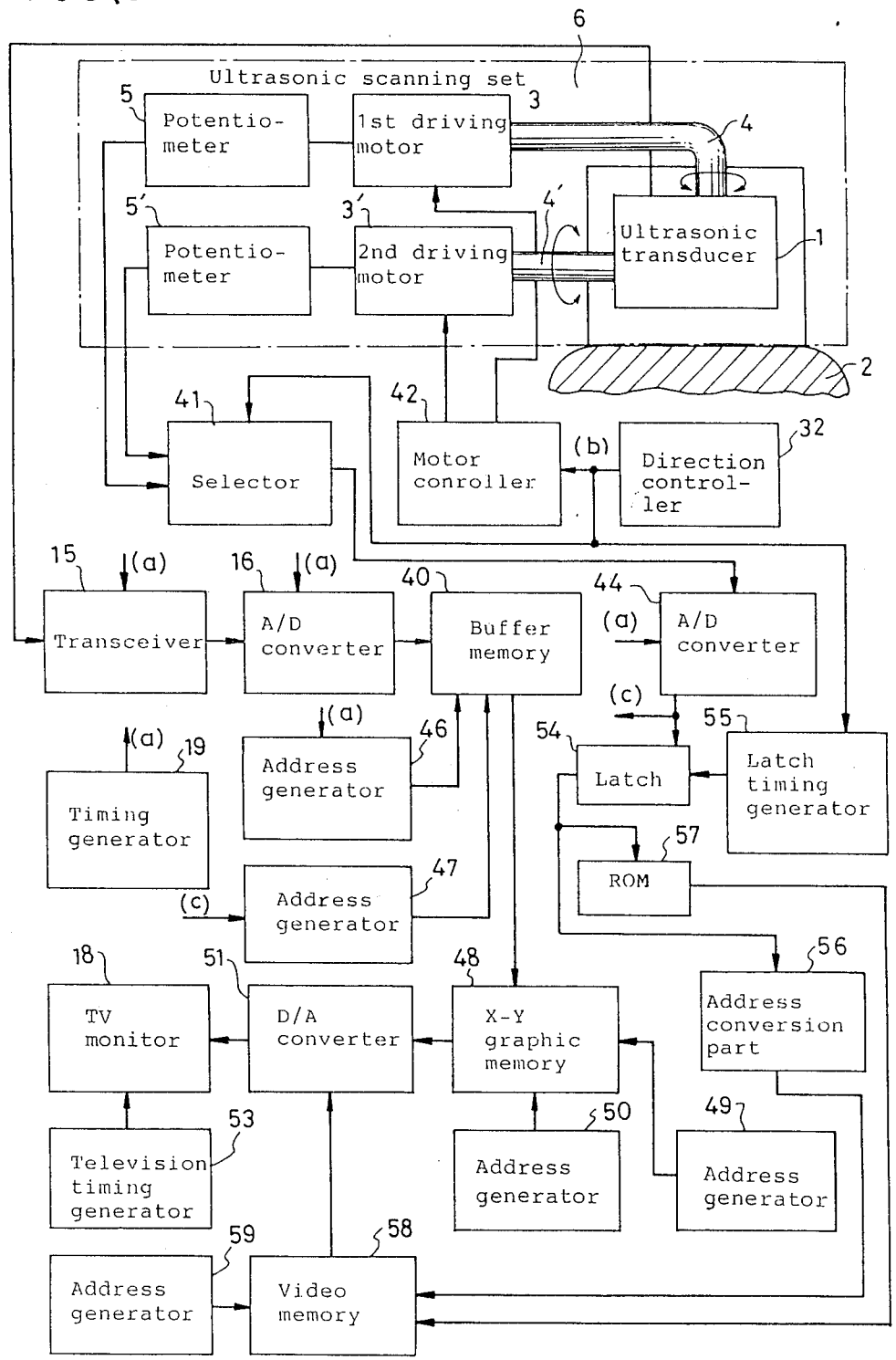
FIG. 6 is a circuit block diagram of still another embodiment of the ultrasonic tomograph of the present invention.

FIG. 6 shows a thid embodiment, with which two-dimensional ultrasonic tomographic imaging can be obtained.

The embodiment of FIG. 6 has a configuration with an ultrasonic transducer element capable of scanning in two different directions, which are, for instance, substantially at right-angles with each other. That is, the ultrasonic transducer scans one direction on the skin surface, thereby making a tomographic image of the skin by such scanning. The switching of direction controller 32 causes the ultrasonic transducer element to be scanned in a direction perpendicular to the previous scanning direction in order to make another tomographic image. Moreover, the tomographic section planes of the two scannings cross with a certain angle (for instance, with a right angle). Displaying the two ultrasonic tomographic images on a TV monitor or like display screen displays images which are of two different tomographic section planes and is very effective in clinical diagnosis.

The circuit configuration of the third embodiment is shown in FIG. 6, wherein the corresponding parts and components are designated by the same numerals as the foregoing embodiments. The ultrasonic transducer element 1 is mounted to move in a sector scanning manner in two directions using a known joint means, such as axes 4 and 41. The driving in both directions is controlled by a first electric motor 3 and a second electric motor 3', which are controlled by a motor controller 42 responsive to a control signal from direction controller 32. The motion in both directions of the ultrasonic transducer 1 is detected by a first potentiometer 5 and second potentiometer 5', which are connected to the axes 4 and 4' of the first electric motor 3 and of the second electric motor 3', respectively. A selector 41 selects either one of the outputs of the first potentiometer 5 and the second potentiometer 5'. The output of the selector 41 is routed to an A/D converter 44. The direction controller 32 produces a signal to the motor controller 42 and to the selector 41, to select either scanning direction among the above-mentioned two directions, thereby designating direction of the scanning of the ultrasonic transducer 1. The A/D converter 44 corresponds to the A/D converter 7 of the previous embodiment and receives one angle information signal from either the first potentiometer 5 or the second potentiometer 5'. The A/D converter 44 issues a digital-converter angular information signal to a latch 54 in response to the angle information. A transceiver 15 receives a signal from the ultrasonic transducer 1, which corresponds to ultrasonic waves reflected from the object to be examined 2. This signal is routed to an A/D converter 16, which converts the received analog signal from the transceiver 15 to a digital-received signal, in synchronism with the timing signal from a timing signal generator 19. An address generator 46 comprises a counter which operates in synchronism with the timing signal from timing signal generator 19 and generates a signal corresponding to the writing address to be given to a buffer memory 40. The output of the A/D converter 16 is also routed to buffer memory 4. An address generator 47 is for generating a signal corresponding to the reading address to be given to the buffer memory 40 for reading out therefrom. An X-Y graphic memory 48 is for storing information indicative of the ultrasonic tomographic image to be displayed on the TV monitor 18 in two-dimensional disposition with the received signal. An address generator 49 comprises an adder or like circuit to generate a signal corresponding to a writing address which is given to the X-Y graphic memory 48 to instruct the writing of the data stored therein. Further, an address generator 50 generates an address data signal for reading the data stored in X-Y graphic memory 48. A D/A converter 51 is for D/A conversion of the image signal output from the X-Y graphic memory 48 to display on the TV monitor 18. A television timing generator 53 issues timing signals to the TV monitor 18 and also generates timing signals of the address generator 50. The latch 54 retains output data from the A/D converter 44, and receives the data therefrom at a certain timing. A latch timing generator 55 generates a latch timing signal to be supplied to the latch 54. An address conversion part 56 converts data from the latch 54 to predetermined addresses. A ROM 57 is for storing a display format of a positional relation of the ultrasonic tomographic images and a group of address data. A video memory 58 is a memory for storing scanning direction data and positional relation data which are used for displaying on the TV monitor 18. The video memory 58 has a region equivalent to or larger than that of that of the X-Y graphic memory 48. An address generator 59 is for generating an address for reading out the video memory 58 to display the information stored therein on the TV monitor 18.

Now, the operation of the third embodiment is elucidated. Processing of the ultrasonic signal reflected from the object to be examined 2 and transduced by the ultrasonic transducer 1 is substantially the same as that of the foregoing example of FIG. 2. That is, in synchronism with timing signal from the timing signal generator 19, the transceiver 15 intermittently generates a transmit signal to the ultrasonic transducer 1 which is converted to ultrasonic waves thereby. These waves are directed to the object, and the ultrasonic waves reflected by the object to be examined 2 are received by the ultrasonic transducer 1. This converts the ultrasonic wave reflected from the object to electric signals and gives it to the transceiver 15. Then, the transceiver 15 amplifies the electric signal based on the received reflected ultrasonic wave (hereinafter referred to as received signal) and gives it to the A/D converter 16, which converts the received signal to a digital-type signal. Electric signals representing the angular positions of the ultrasonic transducers 1 in the first direction of scanning and in the second direction of scanning are produced by the potentiometers 5 and 5', respectively. One of the driving motors 3 and 3' is selected for driving the ultrasonic transducer 1 by motor controller 42 which is controlled by an output signal in the direction controller 32. The motor controller 42 receives the "0" or "1" of the selection signal (b) and drives the motor(s) corresponding thereto. The selection signal (b) is further given to the selector 41, so as to make the selector 41 select a signal from one of the potentiometers 5 or 5' which corresponds to 0 or 1. Then, the output of the potentiometer 5 or 5' is inputted to the A/D converter 44, and is A/D converted in synchronism with the timing signal (a), thereby producing angle signal (c). On the other hand, the received signal which is converted by the A/D converter 16 is led to the buffer memory 40. Then the received signal in the buffer memory is read out therefrom in synchronism with the timing signal (a) at a timing which is different from the writing times in the buffer memory 40, using an address signal produced in the address generator 47, which produces an address signal in a manner that the tomographic image data is aligned based on the angle signal (c) to match the matrix disposition in the X-Y graphic memory 48. The received signal subsequently read out from the buffer memory 40 is written in the X-Y graphic memory 48 in synchronism with the timing signal (c), at the address designated by the address generator 49. For instance, the memories of the X-Y graphic memory 48 can be divided into two parts—data of the received signal taken by the first scanning is stored in the first divided part and the data of the received signal taken by the second scanning is stored in the second divided part. This is possible by limiting the address region of the address generator 49 for writing the X-Y graphic memory, by utilizing the output signal of the direction controller 32. The received signal data stored in the X-Y graphic memory 48 is then read out by the address signal of the address generator 50 which is synchronized with the timing signal generated in the television timing generator 53, and is converted to an analog signal by the D/A converter 51. This enables the display of two ultrasonic tomographic images 60a and 60b on the display screen, e.g. the TV monitor 18 as shown in FIG. 7(A).

Figure 7:
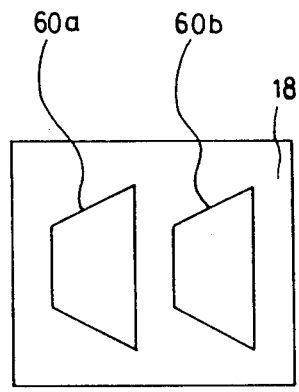
FIG. 7(A), FIG. 7(B) and FIG. 7(C) show an example of a displayed image on the display screen of the embodiment of FIG. 6.
Figure 7:
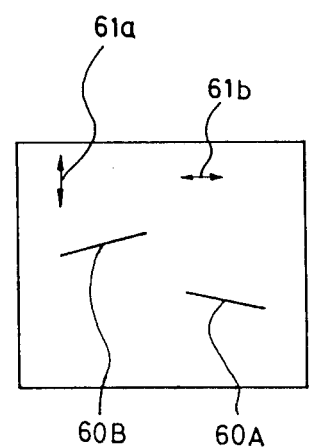
Figure 7:
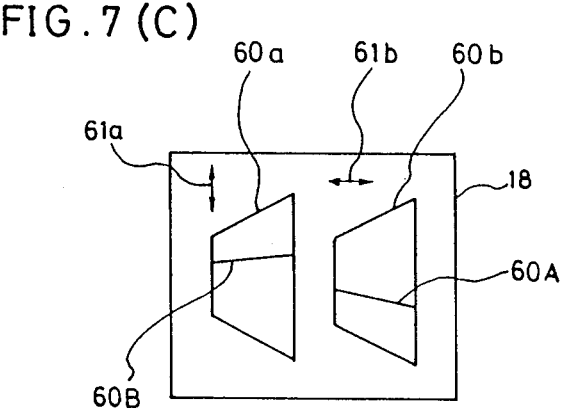

In displaying on the TV monitor 18, besides the two tomographic images 60a and 60b with regard to two different scanning directions, mutual positional relation data for displaying the lines 60B and 60A, which show positions of tomographic section planes for the tomographic images 60b and 60a, respectively, as shown in FIG. 7(B), is displayed in a combined manner as shown in FIG. 7(C). For the purpose of displaying the mutual positional relation data, the data for the mutual positional line are written in the video memory 58 which has an address region corresponding to the X-Y graphic memory 48. In case the region of the tomographic image to be displayed on the display screen 18 is preliminary determined, the data of mutual positional line corresponding to the region are written beforehand; these data are preliminary stored in the ROM 57, and are written in an address corresponding to the addresses generated by the address conversion part 56 by receiving the output signal from the direction controller 32.

Next, a method for displaying for clarity of mutual relations of the two ultrasonic tomographic images 60a and 60b of the two different scanning directions is described with reference to FIG. 8.

Figure 8:
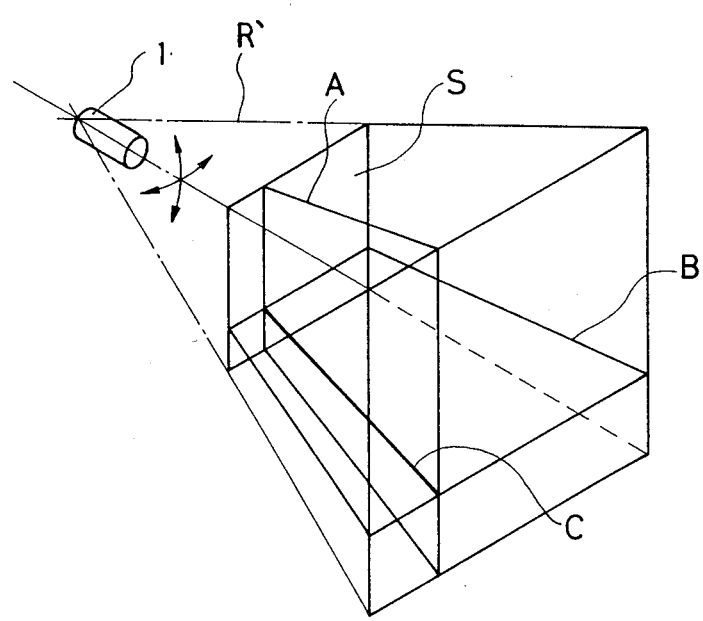
FIG. 8 is a perspective view showing motions of the ultrasonic transducer element with respect to the object skin surface and tomographic planes and the tomographic image on the display screen.

FIG. 8 is a perspective view showing the relation between the ultrasonic scanning regions when the ultrasonic transducer 1 is fixed at a certain direction. Two tomographic images 60a and 60b on the TV monitor 18 are for each other perpendicular tomographic sectional planes A and B of FIG. 8. The planes A and B can be varied to arbitrary positions in the range of truncated pyramid-shaped space R. In order to show the mutual relation between the tomographic sectional planes A and B, images of the crossline which is a crossline of the planes A and B are displayed on the tomographic images 60b and 60a, respectively. To display the crossline C, two angle position data of the potentiometers 5' and 5 when the ultrasonic transducer 1 is at such an angle position to emit the ultrasonic beam thereon are necessary. In order to obtain such two angle position data, the latch 54 latches the output data of the A/D converter 44 at every timing signal (a) of the timing signal generator 19, and sends the latched data to the address conversion part 56. The address conversion part 56 converts the address in synchronism with the output of the latch timing generator 55. The latch timing signal is issued twice whenever driving of the motors 3 or 3' is switched. The output of the potentiometer 5 or 5' to be stopped by reception of the first latch timing signal is sent to the address conversion part 56, and the output of the potentiometer 5 or 5' to be started by the second latch timing signal is sent to the address conversion part 56. The address conversion part 56 detects the scanning direction or the display region of the X-Y graphic memory 48 and the position with respect to the crossline C, and issues address data corresponding thereto. The ROM 57 provides data for writing in the video memory 58 in synchronism with the latch timing signal. Then, the display data written in the video memory 58 is read out by using an address signal from the address generator 59 in synchronism with the timing signal of the television timing generator 53. The read out data from the video memory are assembled in the D/A converter 51 along with the output of the tomographic image data from the X-Y graphic memory 48, and the resultant assembled signal is displayed on the TV monitor 18.

FIG. 7(C) shows the display of the assembled tomographic images 60a and 60b, which are taken by the scanning in the first direction (on the scanning plane A in FIG. 8) and in the second direction (on the scanning plane B in FIG. 8). The assembled tomographic images in FIG. 7(A) are an assembled display consisting of the tomographic image per 60a and 60b in FIG. 7(A) and display the cross sections 60A and 60B, which show positions and directions of the scanning planes A and B on the images 60b and 60a, and arrow marks 61a and 61b which show direction of scannings.

While specific embodiments of the invention have been illustrated and described herein, it is realized that modifications and changes will occur to those skilled in the art. It is therefore to be understood that the appended claims are intended to cover all modifications and changes that fall within the true spirit and scope of the invention.

What is claimed is:

1. An ultrasonic tomograph comprising:
   (1) display means, having two display areas for respectively simultaneous displaying a first and a second tomographic image;
   (2) display marker producing means for producing a display marker which can be moved on said display area of said first tomographic image for designating an area of said first tomographic image to be displayed as said second tomographic image;
   (3) ultrasonic transducer means, for emitting ultrasonic waves to an object to be examined in a sector scanning mode, and for receiving reflected ultrasonic waves which have been reflected from said object;
   (4) driving means for driving said ultrasonic transducer means at first and second scanning angles, respectively corresponding to angles to produce said first and second tomographic images;
   (5) angle detection means for detecting an angle of said ultrasonic transducer means and for producing an angle information signal indicative thereof;
   (6) imaging means for converting said reflected ultrasonic waves from said object of said ultrasonic transducer into image signals;
   (7) address conversion means for compressing said angle information data corresponding to said first tomographic image at a first ratio; and
   (8) memory means, for storing data to display means, said memory means storing: (a) said image data corresponding to said first tomographic image by using said compressed angle information data corresponding to said first tomographic image in a first part thereof, and (b) said image data corresponding to said second tomographic image by using said angle information data not compressed by said address conversion means in a second part thereof.

2. A tomograph as in claim 1 wherein said imaging means produces analog image signals and further comprising first A/D converter means for converting said analog image signals to digital signals, and wherein said angle detection means produces analog angle information signals and further comprising second A/D converter means for converting said analog angle information signal into signal digital information data.

3. An ultrasonic tomograph comprising:
   (1) display means, having two display areas, for respectively simultaneously displaying a first and a second tomographic images;
   (2) display marker producing means for producing a display marker which can be moved on said display area of said first tomographic image, for designating an area to be displayed as said second tomographic image;
   (3) ultrasonic transducer means for emitting ultrasonic waves to an object to be examined in a sector scanning mode and for receiving reflected ultrasonic waves which have been reflected from said object;
   (4) driving means for driving said ultrasonic transducer at first and second scanning angles, respectively corresponding to angles to produce said first and second tomographic images;
   (5) angle detection means for detecting an angle of said ultrasonic transducer means and for producing analog angle information signals;
   (6) imaging means for converting said reflected ultrasonic waves from said object of said ultrasonic transducer to analog image signals;
   (7) first A/D converter means for converting said analog image signals of said imaging means into digital image data;
   (8) second A/D converter means for converting said analog angle information signals of said angle detection means into digital angle information data;
   (9) address conversion means for compressing said digital angle information data from said second A/D converter means corresponding to said first tomographic image at a first predetermined ratio;
   (10) memory means for storing: (a) in a first part thereof, said digital image data of said first A/D converter means corresponding to said first tomographic image by using said compressed digital angle information data from said second A/D converter means corresponding to said first tomographic image, and (b) in a second part thereof, said digital image data of said first A/D converter means corresponding to said second tomographic image by using said digital angle information data of said second A/D converter means without said compressing said data being used for displaying on said display means;
   (11) timing signal generator means for generating a timing signal to be used for controlling said ultrasonic transducer means, said driving means, said angle detecting means, said transfer means, said first and second A/D converter means, said address conversion means, and said memory means;
   (12) an address data correction means having:
   (a) first latch means for storing a value corresponding to data indicative of a start angle of sector scanning by said ultrasonic transducer means;
   (b) second latch means coupled to said timing signal generating means for storing a changing value which is initially equal to said value stored in said first latch means, and includes means for incrementing said changing value by a certain value each time said timing signal is produced by said timing signal generating means;
   (c) third latch means for storing a value corresponding to angle data of an end angle of sector scanning of said ultrasonic transducer means;

(d) first comparator means for comparing said digital angle information data with said value stored in said first latch means and for producing an output indicative of said value stored in said first latch means when said digital angle information data is less than or equal to said value stored in said first latch means;

(e) second comparator means for comparing said digital angle information data with said value stored in said second latch means and for issuing a control signal when said digital angle information data is greater than said value stored in said second latch means;

(f) third comparator means for comparing said digital angle information data with said value stored in said third latch means and for issuing a signal for shifting said value stored in said second latch means to a value corresponding to said value stored in said first latch means when said digital angle information data is greater than said value stored in said third latch means; and (g) means for providing said certain value to said incrementing means when said second comparator means issues said control signal.

4. An ultrasonic diagnosis apparatus comprising:

an ultrasonic scanning set having:

an ultrasonic transducer means, for emitting ultrasonic waves to an object to be examined in a sector scanning mode and receiving a reflected wave thereof;

an electric motor for driving said ultrasonic transducer;

angle detection means for generating an angle signal corresponding to an angle of said ultrasonic transducer means;

ultrasonic transceiver means for providing an ultrasonic signal to said ultrasonic transducer means and receiving a received signal based on a reflected ultrasonic wave from said object to be examined;

a first A/D converter for A/D converting said received signal;

a second A/D converter for A/D converting said angle signal;

compressed data operation means for producing compressed data corresponding to a selected divided scanning range, based on said output of said first and second A/D converters;

address conversion means for producing converted addresses corresponding to said selected divided scanning range; and display means for displaying at least a tomographic image produced by utilizing image data which is read out using said converted address.

5. An ultrasonic diagnosis apparatus comprising:

an ultrasonic scanning set having:

ultrasonic transducer means for emitting ultrasonic waves to an object to be examined in a sector scanning mode and receiving a reflected wave thereof;

a first electric motor for driving said ultrasonic transducer means in a first scanning direction;

a second electric motor for driving said ultrasonic transducer in a second scanning direction;

first angle detection means for generating a first angle signal responding to angle of said first scanning of said ultrasonic transducer;

a second angle detection means for generating a second scanning of said ultrasonic transducer means;

motor control means for controlling said first and second motors;

display means for storing said received signal from said ultrasonic transducer in a graphic memory, and for displaying two ultrasonic tomographic sectional planes by utilizing said received signal;

address conversion means for producing a converted address corresponding to said selected divided scanning range, corresponding to said first angle signal and said second angle signal; and a ROM which stores displaying information as a function of address corresponding to said converted address generated by said address conversion means, and for providing said displaying information to said display means.

* * * * *